United States Patent [19]

Tamiya

[11] 4,033,724
[45] July 5, 1977

[54] OXYGENATOR HAVING A VARIABLE CAPACITY OXYGENATING TUBE

[75] Inventor: Tatsuo Tamiya, Chiba, Japan

[73] Assignee: Senko Medical Instrument Mfg. Co. Ltd., Tokyo, Japan

[22] Filed: June 10, 1975

[21] Appl. No.: 585,633

[30] Foreign Application Priority Data

May 15, 1975 Japan .................. 50-64506[U]
June 2, 1975 Japan .................. 50-74528[U]

[52] U.S. Cl. .................. 23/258.5 BH; 128/DIG. 3; 261/DIG. 28
[51] Int. Cl.² .................. A61M 1/03
[58] Field of Search .................. 23/258.5 A, 258.5 B, 23/258.5 BH; 128/DIG. 3, 274; 195/1.8, 127; 261/DIG. 28; 137/576, 577; 222/553

[56] References Cited

UNITED STATES PATENTS

| | | | |
|---|---|---|---|
| 1,219,265 | 3/1917 | Denhard | 137/577 |
| 1,633,074 | 6/1927 | De Mott | 128/274 |
| 1,845,343 | 2/1932 | Salerni | 128/274 |
| 3,101,083 | 8/1963 | Hyman | 23/258.5 B |
| 3,547,591 | 12/1970 | Torres | 23/258.5 B |
| 3,615,238 | 10/1971 | Bentley et al. | 23/258.5 BH |
| 3,662,710 | 5/1972 | Pankoke et al. | 137/577 |
| 3,764,271 | 10/1973 | Brumfield | 128/DIG. 3 |
| 3,769,162 | 10/1973 | Brumfield | 23/258.5 BH |

FOREIGN PATENTS OR APPLICATIONS

989,821 5/1951 France .................. 23/258.5 B

OTHER PUBLICATIONS

Lopez-Belio et al.; "High Output Bubble Oxygenator. . ."; Surgery, vol. 47, No. 5; 5-60; pp. 772-783.
Page et al.; "Clinical Evaluation of . . . Oxygenator"; J. of Thor. & Card. Surgery, vol. 67, No. 2; 2-74; pp. 213-220.

*Primary Examiner*—Morris O. Wolk
*Assistant Examiner*—Bradley Garris
*Attorney, Agent, or Firm*—William Anthony Drucker

[57] ABSTRACT

An oxygenator (artificial lung) comprising a blood storage tube of an elongated cylindrical configuration; an oxygenating tube of an elongated cylindrical shape longitudinally inserted through said blood storage tube and having a central portion of its lower end provided with an oxygen injection means with a built-in perforated plate and having said lower end provided with blood inlet ports; a blood capacity control means provided at an upper portion of said oxygenation tube and including a rotatable cylinder and side openings; a debubbling chamber formed in an upper portion of said blood storage tube; and a blood storage chamber (reservoir) defined by a lower portion of said blood storage tube and incorporating a heat exchanger.

4 Claims, 2 Drawing Figures

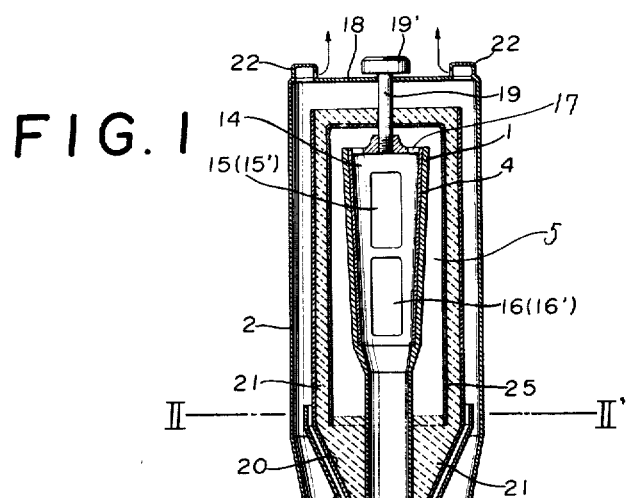
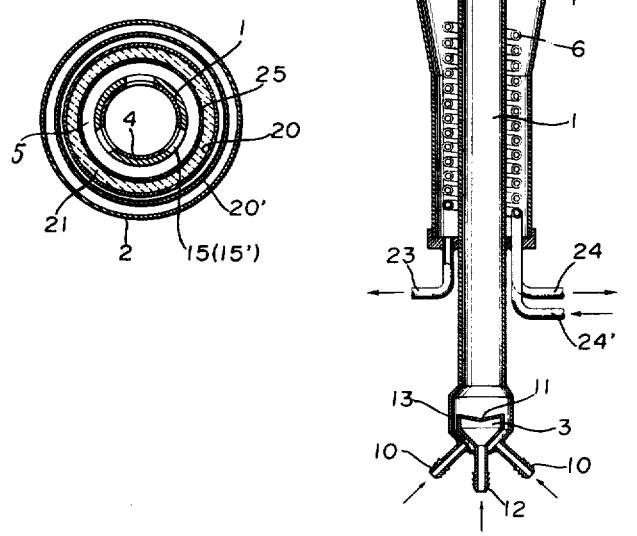

OXYGENATOR HAVING A VARIABLE CAPACITY OXYGENATING TUBE

BACKGROUND OF THE INVENTION

1. Field of the Invention

The present invention relates to improvements in or to blood oxygenators.

2. Description of the Prior Art

The artificial lung or blood oxygenator is usually used for intracardiac surgery. Its primary role is to substitute for respiratory function, that is, blood gas exchange.

With aid of a pump, this apparatus mains the blood circulation throughout the whole human system, regardless of cardiac conditions, such as arrest, cardiotomy and so forth.

Such an artificial circulatory operation is called extracorporeal circulation. In the conventional method, with the above-mentioned devices, a large amount of the blood was required to prime the whole apparatus, and many blood donors were necessary to conduct intracardiac surgery. This frequently caused the homologous blood syndrome (a kind of antigen-antibody reaction intensified by such as artificial perfusion), and postoperative serum hepatitis.

In recent years, there has been provided a reduction in the priming blood volume so that the bubble oxygenator is re-recognized for its practical value. Many attempts have been made to compact the apparatus. At the present time, however, there have yet been unsettled problems in the priming volume, trauma to the blood components, etc.

Further, some of commercialized oxygenators have an oxygenating tube of partitioned structure to prevent collection of bubbles in the upper portion, when the tube tipped, and moreover some of them have baffle boards to promote oxygenation of blood by stirring. However, such structures cause disadvantages as mentioned below. The partitioned structure is prone to further agglomeration of the oxygen bubbles and separation of the bubbles from blood, while insertion of baffle boards in the tube is liable to cause excessive stirring of the blood resulting in hemolysis thereof. Still further, the oxygen demand by each individual is different according to the patient, that is, to their parameters such as the body weight, body temperature, etc. Supersaturation of blood promotes denaturation of the plasma or destruction of blood cells which causes embolism of various types. On the contrary, insufficient oxygenation of the blood brings the patient into a hypoxic state which often gives ill-effects upon his convalescence.

The oxygenator according to the prior skill had the disadvantage that oxygenators of various sizes had to be prepared so as to comply with the blood demands or body weights of each patient (the circulating blood volume is approximately 1/13 of the body weight). Another disadvantage is that if the mesh which surrounds debubbling material is too small, microparticles of larger size may be caught in the mesh to clog, and inversely if the mesh is too large, micro particles such as of smaller size, may pass through the mesh. To prevent such phenomena, a special filter was required in the blood circuit of the conventional oxygenator. However, most of the microfilters commercialized are prone to be clogged, which increases the resistance of the blood flow, with destruction of the blood cells. In addition there have been some problems in the heat-exchanger for thermo-conduction.

A first object of the present invention is to provide an oxygenator of compact structure which secures a low-priming volume perfusion.

A second object of the invention is to provide an oxygenator which maintains adequate oxygenation with least blood trauma.

A third object of the invention is to provide an oxygenator which is equipped with a capacity-control-device of the oxygenating tube to meet the oxygen requirement varied with patient parameters.

A fourth object of the invention is to provide an oxygenator which is equipped with (duplicate) microfilter of gravity drainage that consists of one relatively coarse mesh enveloping (over) the debubbling chamber and of one or more than one fine mesh covering over a lower portion of the coarse mesh; no conventional filter is required in the blood circuit thereof.

A fifth object of the invention is to provide an oxygenator which is equipped with blood reservoir that incorporates a heat exchanger.

Other and further objects of this invention will become obvious upon an understanding of the illustrative embodiment about to be described or will be indicated in the appended claims, and various advantages not referred to herein will occur to one skilled in the art upon employment of the invention in practice.

BRIEF DESCRIPTION OF THE DRAWINGS

FIG. 1 is a central longitudinal sectional view showing an embodiment of the oxygenator according to present invention, and FIG. 2 is a cross sectional view showing part of the oxygenator taken along line II—II of FIG. 1.

DESCRIPTION OF THE PREFERRED EMBODIMENT

Reference numeral 1 designates an oxygenating tube in a cylindrical shape made of transparent hard synthetic resin. On the lower end of the oxygenation tube are provided blood flow inlets 10 and oxygen injection means 3, while the upper portion of the tube is formed with a blood capacity control means 4. The oxygen disperser 3 is nearly in the shape of a wine cup or an inverted cone, on the upper surface of which is provided a cover-like perforated plate 11 of a concave shape (The upper surface of the plate is downwardly recessed). Over the surface of this perforated plate are uniformly formed a number of small pores (the diameter may range from $100\mu$ to $250\mu$) in the arrangement of concentric circles.

On the lower end of the oxygen injection means 3 is mounted an inlet port 12 for oxygen which is in communication with the means 3. Venous blood which passed through the blood inlet ports 10 provided on the lower end of the oxygenation tube 1 into said tube 1 flows slightly centripetally in the upward direction of the perforated dispenser plate 11 through annular space 13 between the oxygen 3 and the inner wall of the oxygenating tube 1.

To enhance the contact of oxygen bubbles with the venous blood a means for slightly sqeezing the oxygen injection may be provided in the oxygenating tube 1, for example at a portion thereof a little above the disperser 3 for squeezing the chamber wall. However, in view of the facts that also the oxygen disperser 3 may be made so as to be capable of controlling its own injection for parging the extend of oxygenation of the blood, and that the venous blood flows slightly centripetally into the tube 1, the oxygenator has to be of such a structure as to eliminate any noxious influence caused by the positive stirring action of a mixer which is liable to cause hemolysis, for example, turbulence of the blood flow due to the insertion of baffle boards. Further, the oxygenating capacity of the oxygenating tube 1 is roughly proportional to the capacity of the same tube itself provided the injecting amount of the oxygen disperser 3 is constant. Therefore, the oxygenator according to the present invention includes a blood capacity control means 4 which is of a simple construction and is capable of varying the blood capacity of the oxygenation tube 1 in simple manner in accordance with the oxygen demand of the patients so as to always keep the oxygen content of the blood at an adequate lever. Said blood capacity control means 4 comprises an internal cylindrical member 14 rotatably inserted in the upper half of the interior of the oxygenation tube 1. The side walls of both the upper portion of the oxygenation tube 1 and the cylindrical member 14 are formed with pairs of outer and inner side openings 15, 15' and 16, 16' in a two-step or two-rank arrangement. By rotating the internal cylindrical member 14, the blood capacity of the oxygenating tube can be controlled in such a manner that each pair of the inner and outer side openings 15, 15' and 16, 16' may be brought into alignment with each other or become opposite each other, or may be deviated from their aligned position. In the case of the means 4 being a two-step or rank type, there is no difficult problem in designing the size and position of the side openings in the side walls of the inner cylindrical member 14 and the oxygenating tube 1. But, in the case of three-step changeover type, it is necessary to design them so that the paired upper and lower side openings are formed in a suitably transversely deviated relationship with each other, or that they differ in shape or size to each other, for obtaining the below-mentioned effect. Hereunder described is how to vary the blood capacity by the use of the three-step changeover mechanism: By rotation of the internal cylinder 14 the lower side openings 16, 16' are brought into alignment with each other so that when the level of the blood in the internal cylinder reaches the lower edges of the side openings 16, 16', the blood over said lower edges flows out through the side openings. Thus, in this position, the blood capacity of the oxygenation tube 1 is the samllest. Next, by further rotating the internal chamber 14 until the side openings 16, 16' are completely closed, the upper side openings 15, 15' are now brought into alignment with each other, so that the level of the blood in the tube comes up to reach the lower edges of the side openings 15, 15'. Then, when the internal cylinder 14 is further rotated until both the upper and lower side openings become completely closed, the blood capacity of the oxygenating tube 1 reaches its maximum value, and then an excess of the blood (i.e., part of the blood over the edges) flows out through an aperture 17 in the upper end of tube 1. On each step, plural pairs of inner and outer side windows are provided at equi-intervals:

Oxygenators having two or three pairs of side windows per step are used. The internal cylindrical member 14 has its upper end secured to a central rotary shaft 19, and by rotating the knob 19' of the shaft 19 located outside, the internal cylinder 14 can be freely rotated. And, the internal cylinder 14 and the upper half of the oxygenizing tube 1 are both formed in inverted cones with gentle slopes so as to increase the volume of the capacity control means at a fixed height of the cylinder and also facilitate the rotation of the internal cylinder 14. As shown in FIG. 1, the oxygenation of tube 1 is longitudinally inserted in a blood storage tube 2 in coaxial relation thereto. The blood storage tube 2 is made of transparent hard synthetic resin and takes the form of an elongated annular cylinder, the upper half of which is formed with a debubbling chamber 5 therewithin, while the lower half is formed in an inverted cone to serve as a blood storage chamber 7 incorporating a heat exchanger 6. Said debubbling chamber 5 is composed of a larger mesh-sized mesh, a microfilter 20 (made of polyester for example) which is partitioned around the upper half of the oxygenation tube 1 within which the capacity control means 4 is arranged, and the mesh enveloped the means 1 and the tube 1 in moderately spaced relation therefrom, and the lower portion of said larger mesh-sized mesh 20 is further enveloped in moderately spaced with one (or more than one) mesh, i.e., another microfilter 20' (made of polyester for example) having smaller mesh-size than that of the mesh 20. Said debubbling chamber 5 includes a debubbling material 21 filled the mesh 20 and the capacity control means 4 (or the upper half of the tube 1). Said meshes 20, 20' may be made of artificial fiber such as nylon etc.

Of these meshes, outer one 20' has finer mesh (desirably or size ranging from $50\mu$ to $25\mu$,), and inner one 20 has a rough mesh (of a size ranging from $100\mu$ to $60\mu$). As the debubbling material a filementous material of polypropylene is used which has been subjected to antifoam coating. A support member 25 for supporting the debubbling chamber is disposed between said two meshes 20, 20' and the capacity control means 4 to envelope the whole capacity control means 4. This member 25 serves to keep said capacity control means 4 (or the upper half of the oxygenation tube 1) and debubbling chamber 5 in suitably spaced relation to each other, and prevent deformation of the debubbling chamber 5, and also instrusion of the debubbling material 21 through the side openings 15, 15', 16, 16' into the capacity control means 4 which may impede the rotation of the internal cylinder 14. The support member 25 has a roughly meshed structure and is made of a synthetic resin.

Since the debubbling chamber 5 is thus constructed, oxygen bubbles contained in the blood flowing from the oxygenation tube 1 vanish immediately when they come in touch with said debubbling material. Thus, so-called arterial blood free of bubbles is obtained.

An excess of gas of oxygen or carbon dioxide or the like is discharged through exhaust holes 22 provided in the upper cover 18 of the blood storage tube 2.

The arterial blood debubbled through the debubbling chamber 5, is now fallen into the blood storage chamber 7 in the shape of an inverted cone after passing the meshes 20, 20'. After passing the debubbling chamber 7, the arterial blood is then delivered to a feed pump (not shown) through an outlet pipe 23.

At the lower portion of the blood storage chamber 7 is provided a heat exchanger 6 composed of fine metal pipe 24, 24' spirally wound around the oxygenating tube.

Both ends of the metal pipe are connected to a constant temperature oven (not shown), and through said metal pipe is flowed cold water or hot water for cooling or warming blood in the neighborhood of the heat exchanger. As said heat exchanger 6, one composed of an alumite fine pipe can exhibit much higher effectiveness than conventional ones (namely, about twice as high as that of a Temptrol (trade mark) typed drum oxygenator per unit area). But, any other like metal may be suitable for the heat exchanger.

In this case with the filtering function of said larger mesh-sized mesh 20 (inner side) larger alien substances can be eliminated, and with that of finer mesh 20' (outer side) smaller alien substances such as micro bubbles of oxygen can be easily eliminated. Further, since the upper half of the debubbling chamber 7 is enveloped only with larger mesh-sized mesh 20, in case of being clogged at the lower portion of the debubbling chamber 5 enveloped with plurality of meshes 20 and 20', debubbled arterial blood can be dropped through said larger mesh-sized mesh 20 of the upper portion thereof.

That is, the upper half of the debubbling chamber 7 enveloped with only one larger mesh-sized mesh 20 also serves as a safety valve.

As evident from the foregoing description, according to the present invention, the oxygen provided at the lower end of the oxygenation tube comprises a perforated plate 11 which has a concave section for homogenous production of oxygen bubbles around the entire margin of the disperser, and the surface of which is formed with a number of small pores which are sparsely distributed over the surface. By virtue of such construction, agglomeration of oxygen bubbles which may lead to reduce oxygenaging efficiency of the blood, can be effectively prevented. Besides, even when the oxygenating tube 1 happens to be somewhat tipped, the oxygen injection device is capable of uniformly producing oxygen bubbles thus to ensure proper oxygenation of the blood. Further, since a capacity control device is provided in which the rotation of the internal cylinder which automatically change the positional correlation of the inner windows with outer windows can vary the capacity of the oxygenating tube multistepwisely, it is feasible to always keep the blood properly oxygenated in accordance with the oxygen demand of each patient, as stated before. Still further, since the lower half of the blood storage portion 2 is configurated in an inverted cone, it is easily possible to maintain the level of the blood within the oxygenation tube at least above a fixed critical level, even when the blood in the oxygenating tube has decreased in quantity. Accordingly, the priming volume is markedly reduced. This therefore, makes it unnecessary to collect a large amount of blood to conduct intracardiac surgery as in conventional cases. There will be few who develop the homogenous blood syndrome after intracardiac operation in which the oxygenator according to the invention is used. Moreover, postoperative serum hepatitis can be markedly reduced.

Still further, another remarkable feature is that since the debubbling chamber is defined with one larger mesh-sized mesh (course mesh) and at the lower portion of the chamber with plurality of meshes. Accordingly, relatively larger alien substances in arterial circuit such as aggregation of thrombocytes, leucocytes, fibrin, fat particles, tissue, etc., can be eliminated with filtering function of the inner coarse mesh, while minute alien substances such as minute air bubbles, oxygen bubbles, relatively fine blood components, and minute chips of the debubbling material can be easily removed with filtering function of the outer rough mesh(es). And further even if the lower half of the debubbling chamber being clogged by the alien substances, blood can fall into the blood storage chamber through the coarse mesh enveloping the upper half thereof so that it is unnecessary to employ and forced filtration in the blood circuit which has been a cause for the increase in pressure or obstruction in the arterial circuit, and the destruction of the blood cells, so that the oxygenator of the present invention is very reliable and compact in size.

While there has been described what is at present considered to be the preferred embodiment of the invention, it will be understood that various modifications may be made therein, and it is intended to cover in the appended claims all such modifications as fall within the true spirit and scope of the invention.

What is claimed is:

1. An oxygenator comprising:
    a blood storage tube of a cylindrical shape;
    an oxygenating tube longitudinally inserted in said blood storage tube in coaxial relation thereto;
    at least one blood inlet port provided at a lower end of said oxygenating tube;
    an oxygen disperser, provided within a central portion of the lower end of said oxygenating tube, including an injection plane composed of a perforated plate of a concave section, having a downwardly recessed surface;
    a debubbling chamber provided within the annulus formed by said blood storage tube and said oxygenating tube and disposed at the upper portions thereof
    a blood storage chamber defined by a substantially lower portion of said blood storage tube;
    a heat exchanger wound around said oxygenating tube in said blood storage tube;
    a blood capacity control means including an uppermost blood outlet at the top of said oxygenating tube and at least one outer side opening provided in a side wall of the substantially upper portion of said oxygenating tube and at least one corresponding inner side opening provided in a side wall of an internal cylindrical member rotatably longitudinally inserted in said substantially upper portion of said oxygenating tube, wherein, by rotating the internal cylindrical member, each pair of said outer and inner side openings are brought into alignment with each other thereby creating a lower blood outlet or deviated from their aligned positions thereby providing for the flow of blood through said uppermost outlet whereby the blood capacity of said oxygenating tube is controlled.

2. The oxygenator as claimed in claim 1, wherein said blood capacity control means includes a first pair of said inner and outer side openings and a second pair of said inner and outer side openings, said first and second pairs being vertically disposed one above the other.

3. The oxygenator as claimed in claim 1, wherein said debubbling chamber is enveloped with a coarse mesh and at the lower half thereof with at least one finer mesh which partially envelopes said coarse mesh.

4. The oxygenator as claimed in claim 1, wherein said substantially upper portion of said oxygenating tube and said internal cylindrical member are in the shape of inverted cones, respectively.

* * * * *